United States Patent
McKee et al.

(10) Patent No.: US 8,930,028 B2
(45) Date of Patent: Jan. 6, 2015

(54) HANDHELD MEDICAL DEVICE FUNCTIONALITY WITHOUT BATTERY

(75) Inventors: Michael C. McKee, Arlington Heights, IL (US); Michael G. Nicholas, Wheeling, IL (US); Blaine E. Ramey, Indianapolis, IN (US)

(73) Assignee: Roche Diagnostics Operations, Inc., Indianapolis, MN (US)

( * ) Notice: Subject to any disclaimer, the term of this patent is extended or adjusted under 35 U.S.C. 154(b) by 73 days.

(21) Appl. No.: 13/559,648

(22) Filed: Jul. 27, 2012

(65) Prior Publication Data

US 2014/0031657 A1 Jan. 30, 2014

(51) Int. Cl.
*G06F 1/16* (2006.01)

(52) U.S. Cl.
USPC .................. 700/266; 702/19; 702/22; 702/31; 702/32; 600/365

(58) Field of Classification Search
CPC ................... A61B 2560/0204; A61B 5/14532; A61B 2560/0214
USPC ............ 700/266; 702/19, 22, 31, 32; 600/365
See application file for complete search history.

(56) References Cited

U.S. PATENT DOCUMENTS

2009/0318779 A1* 12/2009 Tran .............................. 600/301

FOREIGN PATENT DOCUMENTS

GB 2474261 4/2011
WO WO2010/040090 4/2010

OTHER PUBLICATIONS

Battery Charging Specification, Revision 1.2 (Dec. 7, 2010).
"i.MX233 Power Management Unit and Battery Charger" Freescale Semiconductor, Inc. (2009).

* cited by examiner

*Primary Examiner* — Shogo Sasaki
(74) *Attorney, Agent, or Firm* — Harness, Dickey & Pierce, P.L.C.

(57) ABSTRACT

A processor module includes memory having instructions for executing functions of a handheld diabetes management device and a processor that selectively executes the instructions. Battery terminals electrically connect the processor module with a re-chargeable battery. A receptacle is configured in accordance with a universal serial bus (USB) standard. A component is included for communicating information from the handheld diabetes management device to a user or another device. A multiplexer module relays power from the receptacle to a bus voltage node. A first switching device is connected between the bus voltage node and a second voltage node. The component receives power from the second voltage node. A second switching device is connected between the bus voltage node and a third voltage node. The processor module is directly connected to the bus voltage node and to the third voltage node.

13 Claims, 6 Drawing Sheets

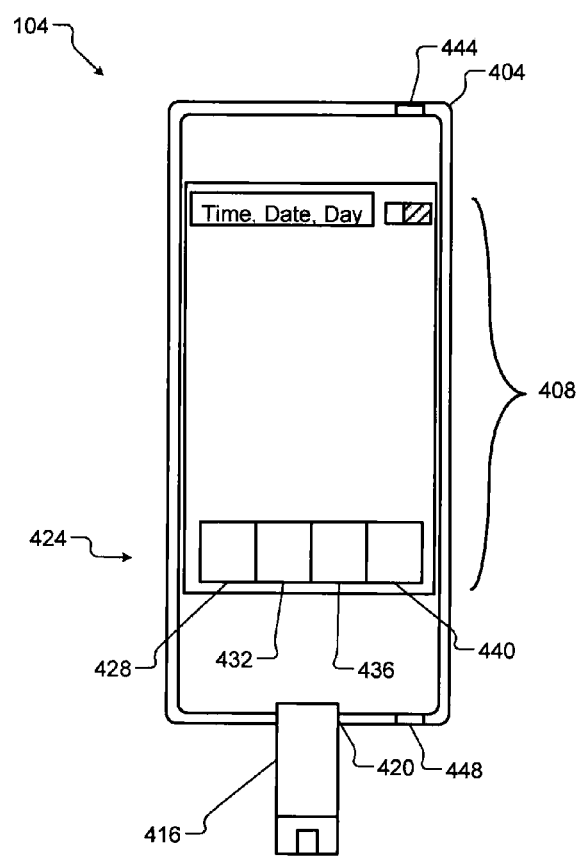
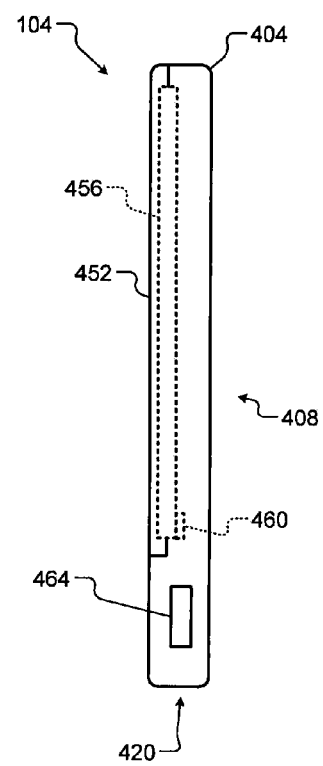
FIG. 4
FIG. 5

HANDHELD MEDICAL DEVICE FUNCTIONALITY WITHOUT BATTERY

FIELD

The present disclosure relates to handheld medical devices and more particularly to functionality of handheld medical devices with and without batteries.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and can be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex because the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors that are unique to each patient. The dynamic nature of blood glucose and insulin, and all other factors affecting blood glucose, often require a person with diabetes to forecast blood glucose levels. Administration of insulin and/or oral medications can be regulated and timed to maintain blood glucose levels within an appropriate range at all times.

Management of diabetes is often highly intrusive because of the need to consistently obtain reliable diagnostic information, follow prescribed therapy, and manage lifestyle on a daily basis. Diagnostic information, such blood glucose level, can be obtained from a capillary blood sample with a lancing device and a test strip. The blood glucose level is measured via the test strip using a handheld blood glucose meter. Interstitial glucose levels can be obtained from a continuous glucose sensor worn on the body.

A therapy regimen for a patient can be established based on one or more of the patient's blood glucose levels. The therapy regimen can include administration of insulin and/or oral medication. Insulin can be administered with a syringe, an insulin pen, an ambulatory infusion pump, or a combination of two or more of the above. With insulin therapy, determining the amount of insulin to inject at a given time can require forecasting meal amount and composition (e.g., of fat, carbohydrates, and proteins, and amounts of each). Determining the amount of insulin to inject at a given time can also require consideration of the effects of exercise and physiologic state. The patient's management of lifestyle factors such as body weight, diet, and exercise can significantly influence the type and effectiveness of therapy.

Management of diabetes involves large amounts of diagnostic data and prescriptive data that are acquired from medical devices, personal health care devices, patient recorded information, health care professional tests results, prescribed medications and recorded information. Medical devices including self-monitoring bG meters, continuous glucose monitors, insulin infusion pumps, diabetes analysis software, and diabetes device configuration software each of which generates or manages or both large amounts of diagnostic and prescriptive data. Personal health care devices can include weights, scales, blood pressure cuffs, pedometers, other activity monitors, and other suitable devices. Patient recorded data can include information relating to meals, exercise, and lifestyle. Health care professional biomarker data can include HbA1C, cholesterol, triglycerides, fasting glucose, and glucose tolerance. Health care professional recorded information can include therapy and other patient-specific information.

Handheld diabetes management devices include one or more batteries that power the handheld diabetes management device. For example, some handheld diabetes management devices include replaceable, standard size batteries and some handheld diabetes management devices include a non-standard sized, re-chargeable battery. Handheld diabetes management devices that include a re-chargeable battery generally include provisions for a connection to one or more external power sources for re-charging the battery.

If the battery is disconnected from a handheld diabetes management device, the handheld diabetes management device is inoperable, even when connected to an external power source. However, a user of the handheld diabetes management device may desire to operate the handheld diabetes management device when the battery is disconnected from the handheld diabetes management device, such as when the battery has been lost. Additionally, it may be necessary to operate the device when the battery is disconnected from the handheld diabetes management device, such as for testing during manufacturing of the handheld diabetes management device. Thus, there is a need for a handheld diabetes management device that is at least partially operable without its battery.

The background description provided herein is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

SUMMARY

In an example, a handheld diabetes management device includes a processor module including memory having instructions for executing functions of the handheld diabetes management device and a processor that selectively executes the instructions. Battery terminals electrically connect the processor module with a re-chargeable battery when the re-chargeable battery is inserted within a battery compartment of the handheld diabetes management device. A receptacle is configured in accordance with a universal serial bus (USB) standard and receives a plug that is configured in accordance with the USB standard. At least one component is included for communicating information from the handheld diabetes management device to one of a user and another device. A multiplexer module receives power via the receptacle when the plug is connected with the receptacle and selectively outputs power to a bus voltage node based on the power received via the receptacle. The processor module is directly connected to the bus voltage node and receives power from the bus voltage node when the re-chargeable battery is not connected to the battery terminals. The at least one component receives power via the bus voltage node when the re-chargeable battery is not connected to the battery terminals. The processor module controls application of power to the at least one component and operation of the at least one component when the re-chargeable battery is not connected to the battery terminals.

In another example, a handheld diabetes management device includes a processor module including memory having instructions for executing functions of the handheld diabetes management device and a processor that selectively executes the instructions. Battery terminals electrically connect the processor module with a re-chargeable battery when the re-chargeable battery is inserted within a battery compartment of the handheld diabetes management device. A receptacle is configured in accordance with a universal serial bus (USB) standard and receives a plug that is configured in accordance with the USB standard. At least one component is included for communicating information from the handheld diabetes management device to one of a user and another device. A multiplexer module receives power via the receptacle when the plug is connected with the receptacle and relays power from the receptacle to a bus voltage node. The processor module is directly connected to the bus voltage node. A first current path is from the battery to the at least one component. A second current path is from the bus voltage node to the at least one component. In response to a determination that the re-chargeable battery is connected to the battery terminals, the processor module enables current flow through the first current path and disables current flow through the second current path. In response to a determination that the re-chargeable battery is not connected to the battery terminals, the processor module disables current flow through the first current path and enables current flow through the second current path.

In yet another example, a handheld diabetes management device includes a processor module including memory having instructions for executing functions of the handheld diabetes management device and a processor that selectively executes the instructions. Battery terminals electrically connect the processor module with a re-chargeable battery when the re-chargeable battery is inserted within a battery compartment of the handheld diabetes management device. A receptacle is configured in accordance with a universal serial bus (USB) standard and receives a plug that is configured in accordance with the USB standard. At least one component is included for communicating information from the handheld diabetes management device to one of a user and another device. A multiplexer module receives power via the receptacle when the plug is connected with the receptacle and relays power from the receptacle to a bus voltage node. The processor module is directly connected to the bus voltage node. A first switching device is connected between the bus voltage node and a second voltage node. The at least one component receives power from the second voltage node. A second switching device is connected between the bus voltage node and a third voltage node. One of the battery terminals is connected to the third voltage node. The processor module is also directly connected to the third voltage node.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 4 is a front view of an example implementation of a handheld diabetes management device;

FIG. 5 is a side view of the example handheld diabetes management device;

DETAILED DESCRIPTION

Figure 1:
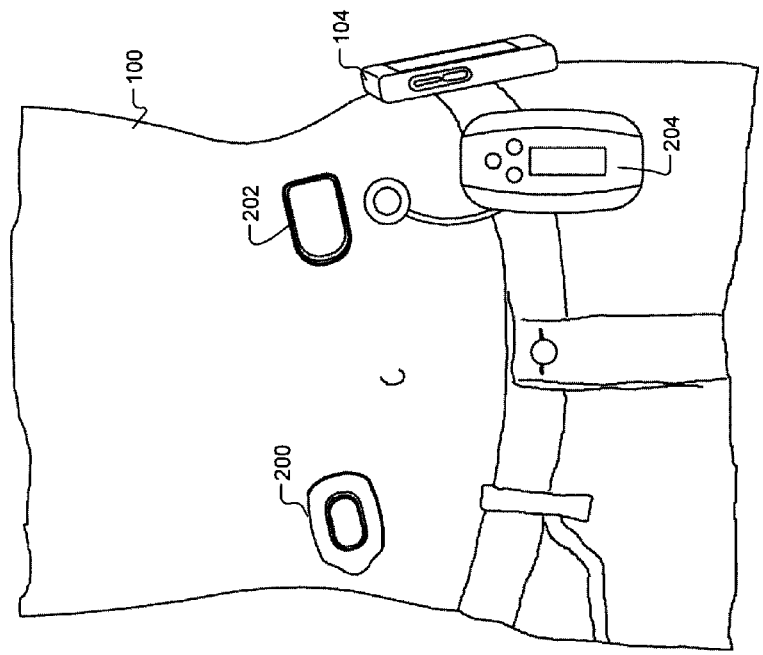
FIG. 1 shows a patient and a health care professional along with various devices that can be used to help the patient monitor and control health.

Referring now to FIG. 1, a patient 100 with diabetes and a health care professional 102 are shown in a clinical environment. The patient 100 with diabetes can be diagnosed with a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 100 typically shares with the health care professional 102 a variety of data including blood glucose (bG) measurements, continuous glucose monitor data, amounts and type of insulin administered, amounts of food and beverages consumed, exercise schedules, health status, and other lifestyle information. The health care professional 102 can obtain additional data for the patient 100, such as measurements of HbA1C, cholesterol levels, plasma glucose, triglycerides, blood pressure, and weight. The data can be recorded manually or electronically on a handheld diabetes management device 104 (e.g., a handheld bG monitor device), a diabetes analysis software executed on a personal computer (PC) 106, and/or a web-based diabetes analysis site. The health care professional 102 can analyze the patient data manually or electronically using the diabetes analysis software and/or the web-based diabetes analysis site. After analyzing the data and reviewing how efficacious previously prescribed therapy is and how well the patient 100 followed the previously prescribed therapy, the health care professional 102 can decide whether to modify a therapy prescribed for the patient 100.

Figure 2:
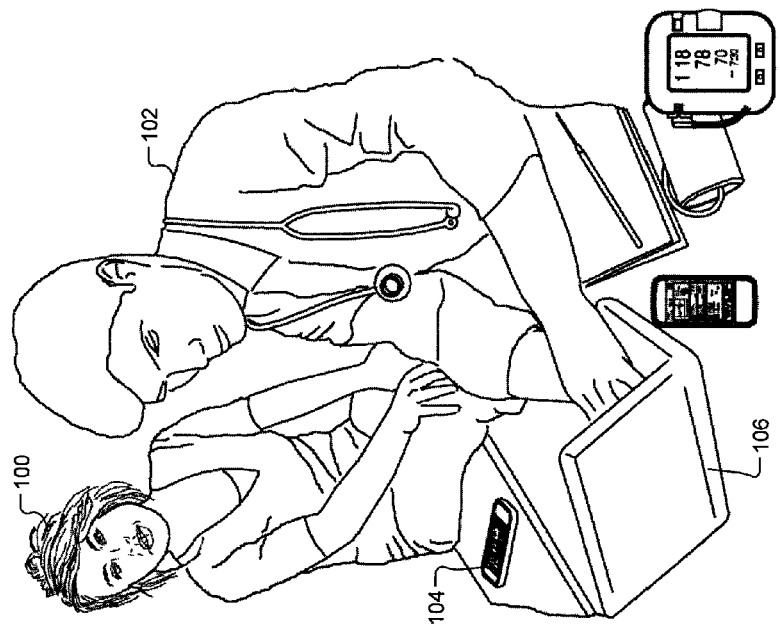
FIG. 2 shows a patient with a continuous glucose monitor (CGM), an ambulatory durable insulin infusion pump, an ambulatory non-durable insulin infusion pump, and a blood glucose (bG) management device.

Referring now to FIG. 2, the patient 100 can use a continuous glucose monitor (CGM) 200, an ambulatory durable insulin infusion pump 204 or an ambulatory non-durable insulin infusion pump 202 (collectively insulin pump 204), and the diabetes management device 104. The CGM 200 can use a subcutaneous sensor to sense and monitor the amount of glucose (e.g., glucose concentration) of the patient 100. The CGM 200 communicates glucose measurements to the diabetes management device 104.

The diabetes management device 104 performs various tasks including measuring and recording bG measurements, determining an amount of insulin to be administered to the patient 100 via the insulin pump 204, receiving user input via a user interface, archiving data, performing structured bG tests, etc. The diabetes management device 104 can transmit instructions to the insulin pump 204, and the insulin pump 204 selectively delivers insulin to the patient 100. Insulin can be delivered in the form of a meal bolus dose, a correction bolus dose, a basal dose, etc.

Figure 3:
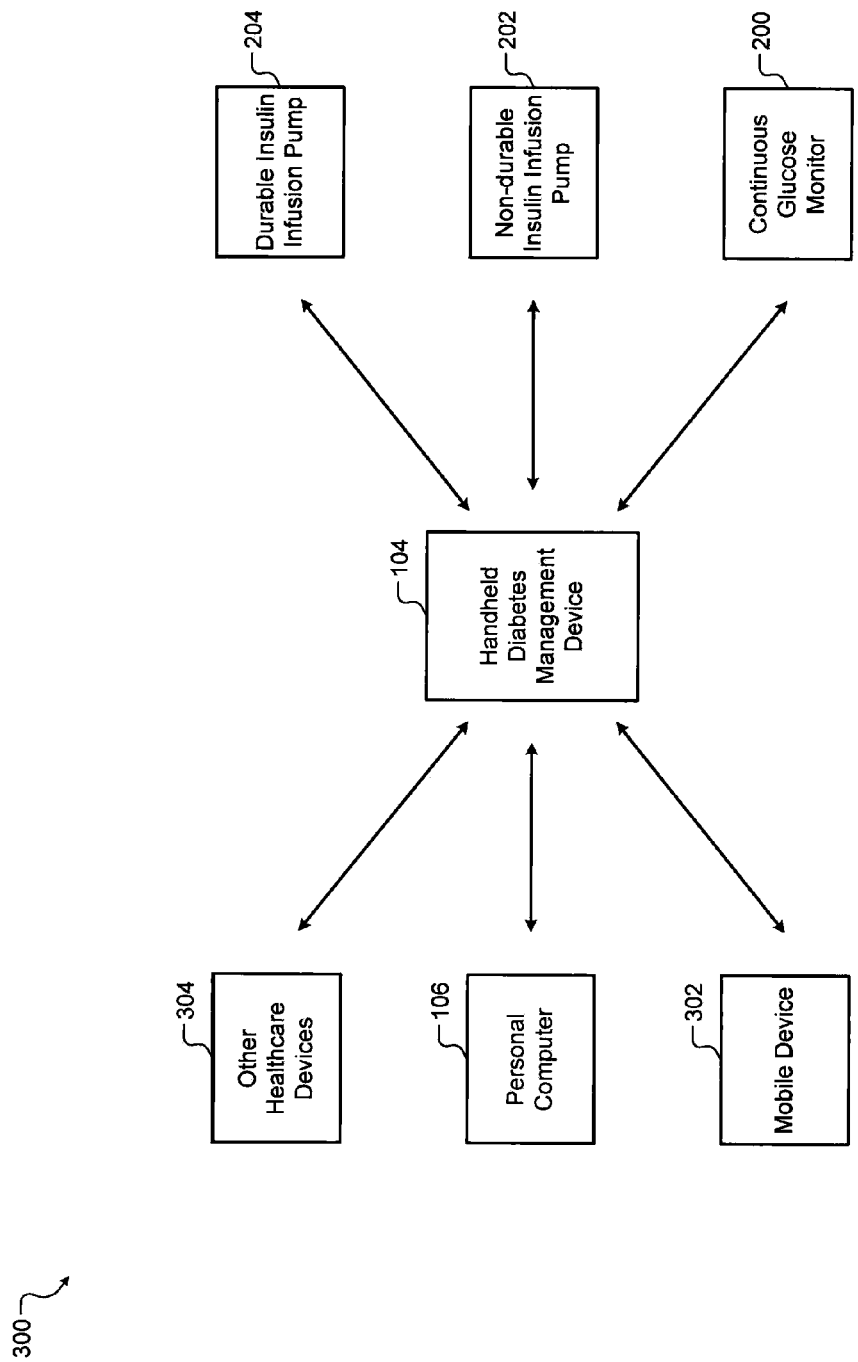
FIG. 3 shows a diabetes care system of systems that can be used to manage diabetes.

Referring now to FIG. 3, a diabetes management system 300 is shown which can be used by the patient 100 and/or the health care professional 102. The system 300 can include one or more of the following devices: the diabetes management device 104, the CGM 200, the insulin pump 204, a mobile device 302, the diabetes management software executed on the computer 106, and one or more other health care devices 304. The diabetes management device 104 can be configured as a system "hub" and communicate with one or more of the other devices of the system 300. The insulin pump 204, the mobile device 302, or another suitable device can alternatively serve as the system hub. Communication between various devices in the system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft HealthVault™ and Google Health™ can be used by the patient 100 and the health care professional 102 to exchange information.

The diabetes management software running on the computer 106 can include an analyzer-configurator that stores configuration information for devices of the system 300. For example only, the configurator has a database to store configuration information for the diabetes management device 104 and the other devices. A patient can interface the configurator through standard web based or computer graphical user interfaces (GUIs). The configurator selectively transmits patient-approved configurations to the devices of the system 300. The analyzer selectively retrieves data from the devices of the system 300, stores the data in a database, selectively analyzes the data, and outputs analysis results through standard web based or computer GUIs.

Referring now to FIG. 4, a high level illustration of an example embodiment of the diabetes management device 104 is presented. The diabetes management device 104 includes, among other things, a housing 404, user unit control switches (not specifically numbered), a touchscreen display 408, and a bG test strip port 420. The user unit control switches, for example, can include ON/OFF switches, volume switches, alarm switches for bG testing and/or insulin administration, and/or one or more other switches or other types of control devices that a patient can use to control functions/operations of the diabetes management device 104.

A bG test strip 416 can be inserted into the bG test strip port 420. The bG test strip 416 can be inserted into the bG test strip port 420 by a patient, from a test strip drum (not shown) located within the housing 404, or in another suitable manner. The bG test strip 416 is shown already inserted into the bG test strip port 420 in the example of FIG. 4.

User selectable options 424 can be displayed on a portion of the display 408. The selectable options 424 can include a menu option 428, a bolus insulin option 432, a carbohydrate option 436, and an event option 440. One or more other user selectable options can additionally or alternatively be available. The patient can access a device menu for the diabetes management device 104 by selecting the menu option 428. The patient can input various insulin (and/or other medication) information (e.g., amount, insulin type, etc.) by selecting the bolus insulin option 432. The patient can input various carbohydrate intake information (e.g., amount) by selecting the carbohydrate option 436. The patient can also input other food intake information (e.g., protein content, fat content, etc.) by selecting the carbohydrate option 436. The patient can input various event related information (e.g., meals, exercise, periods of stress, etc.) that can affect the patient's bG measurements by selecting the event option 440. The patient may access and view a history of events (e.g., of bG measurements, exercise, carbohydrate intake, insulin administration, etc.) via the menu option 428.

Although the display 408 is described herein as a touchscreen display, the diabetes management device 104 can include another suitable form of display (e.g., LED, etc.). If a touchscreen display is not used, the user control switches can include specific buttons or controls by which the patient is able to select various options and input markers needed to operate the diabetes management device 104. The diabetes management device 104 may include one or more visual indicators, such as LED 444. The diabetes management device 104 may include one or more audio output devices, such as speaker 448.

FIG. 5 includes a side view of the example diabetes management device 104. Referring now to FIGS. 4 and 5, the diabetes management device 104 may include a battery compartment 452 for housing a re-chargeable battery 456. The battery 456 may include, for example, a lithium based (e.g., lithium ion) battery or another suitable type of re-chargeable battery. The diabetes management device 104 includes battery terminals 460 for connecting the battery 456 with the diabetes management device 104. The diabetes management device 104 can operate using power drawn from the battery 456.

The diabetes management device 104 can also operate using power drawn from a power source that is external to the diabetes management device 104. The diabetes management device 104 includes a port 464 that is configured in accordance with a universal serial bus (USB) standard. The port 464 is configured to receive a plug (not shown) that is also configured in accordance with the USB standard. The port 464 may be configured to receive, for example, a type-a or a type-b, standard, mini, or micro type USB plug that is configured in accordance with, for example, USB 0.x, 1.x, 2.x, or 3.x standards or another suitable protocol.

When the battery 456 is connected with the battery terminals 460, the battery 456 can be re-charged via power received via the port 464. More specifically, the plug is part of a cable that, at its other end, can be plugged into, for example, a USB port of an adapter that can be plugged into a power source (e.g., a standard wall outlet, a vehicle, etc.) or a USB port of a computer, to receive power. The diabetes management device 104 can operate using power drawn from the battery 456 and/or the port 464 when the battery 456 is connected to the battery terminals 460. When the battery 456 is not connected to the battery terminals 460, the diabetes management device 104 can, at least partially, operate using power drawn via the port 464.

The above description is a broad description of the diabetes management device 104. In practice, the diabetes management device 104 can include additional controls, input ports, output ports, etc., as can be desired to further enhance its utility or its use with other components and devices (e.g., computers, infusion pumps, cellular phones, etc.). The description of the diabetes management device 104 should not be taken as limiting as to the construction of the diabetes management device 104 or as to the features and capabilities of the diabetes management device 104.

Figure 6:
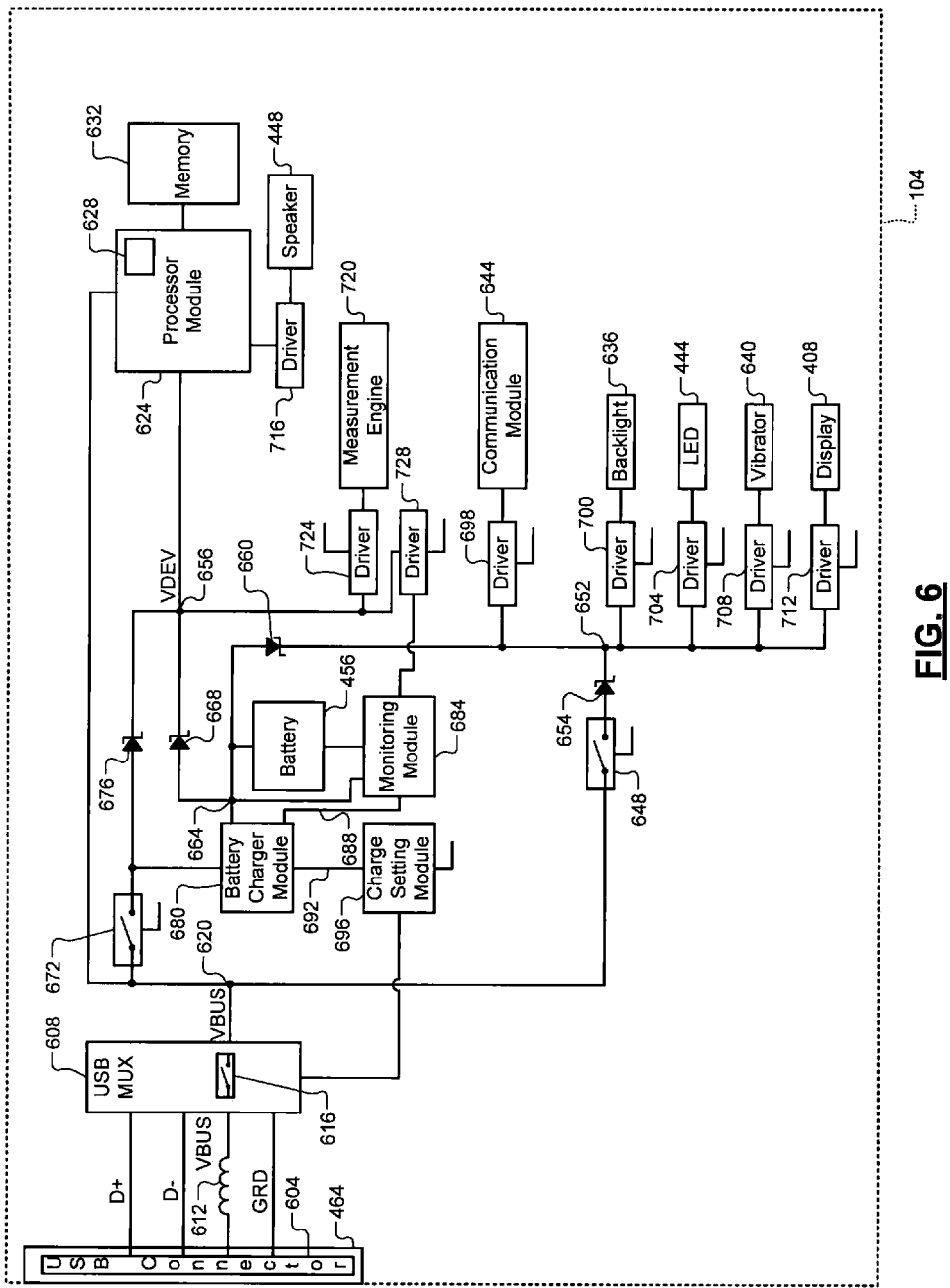
FIG. 6 is a functional block diagram of a portion of the example handheld diabetes management device.

Referring now to FIG. 6, a functional block diagram of a portion of an example implementation of the diabetes management device 104 is presented. The port 464 includes a connector 604 that includes a plurality of pins. Pins of a plug connect with the pins of the connector 604. As illustrated in the example of FIG. 6, the connector 604 may include a bus voltage (VBUS) pin, a ground pin (GRD), and two data pins (D+ and D−). While not shown in the example of FIG. 6, the connector 604 may also include an ID resistor pin that may be used, for example, to identify connection of one or more special types of cables or accessories. The connector 604 may include additional pins in various implementations. The diabetes management device 104 receives and transmits data via the data pins D+ and D−. The diabetes management device 104 receives a bus voltage (VBUS) via the bus voltage pin.

The diabetes management device 104 includes a multiplexer module 608, such as a USB multiplexer, that is connected to the pins of the connector 604. The diabetes management device 104 may include a choke inductor 612 connected between the bus voltage pin and the multiplexer module 608.

The multiplexer module 608 includes a voltage and current protector switch 616. For example only, the protector switch 616 may include a field effect transistor (FET) or another suitable type of switching device. The bus voltage and/or current flow to the multiplexer module 608 may be monitored, and the protector switch 616 may be opened (i.e., open circuited) when the bus voltage is greater than a predetermined voltage and/or the current to the multiplexer module 608 is greater than a predetermined current. This may prevent one or more components of the diabetes management device 104 from being damaged in the event that over voltage and/or over current conditions occur.

When the bus voltage is less than the predetermined voltage and the current to the multiplexer module 608 is less than the predetermined current, the protector switch 616 may be closed. When the protector switch 616 is closed, the multiplexer module 608 outputs the bus voltage to a bus voltage node 620.

The diabetes management device 104 includes a processor module 624 that includes a processor 628. For example only, the processor module 624 may be an i.MX233 applications processor module. Code for executing functions of the handheld diabetes management device 104 is stored in memory 632. While the memory 632 is shown as being external to the processor module 624, the memory 632 may be wholly or partially integrated within the processor module 624.

The processor module 624 is directly connected to the bus voltage node 620. In this manner, in the event that the battery 456 is lost or otherwise not connected to the diabetes management device 104, the diabetes management device 104 can be connected to another power source via the port 464 so a user can still at perform at least some of the functions of the diabetes management device 104.

The diabetes management device 104 includes a plurality of components for communicating between the diabetes management device 104 and one of a user of the diabetes management device 104 and another device (e.g., an insulin pump, a CGM, a computer, etc.). The components that communicate between the diabetes management device 104 and one of a user of the diabetes management device 104 and another device will be referred to as communication components. While examples of communication components are provided, the diabetes management device 104 may include other types of components that communicate information from the diabetes management device 104 to one of a user of the diabetes management device 104 and another device.

For example, the diabetes management device 104 includes the display 408 and one or more visual indicators, such as LED 444, that communicate information to a user of the diabetes management device 104. The diabetes management device 104 may also include a backlight 636 that backlights the display 408 for facilitating communication of information to a user. The diabetes management device 104 may also include a vibrator device 640 which vibrates to communicate information to a user.

The diabetes management device 104 also includes a communication module 644 that communicates with other devices. For example, the communication module 644 may communicate with a computer via the data pins of the connector 604. The communication module 644 may also communicate with other devices, such as wirelessly via one or more antennas (not shown).

When the battery 456 is not connected to the battery terminals 460, the processor module 624 may generally open a first switch 648. The opening of the first switch 648 may be performed, for example, to reduce current drawn from the USB port 464. A reduction in current drawn from the USB port 464 may be required, for example, by a "low or dead battery" provision of a USB charging standard. If connection of a special cable is detected by the multiplexer module 608, for example via sensing a particular value of a resistor connected to the ID pin, the processor module 624 may close the first switch 648 to enable operation without the battery 456. For example only, the first switch 648 may include a field effect transistor (FET) or another suitable type of switching device.

The first switch 648 is connected between the bus voltage node 620 and a second node 652. A first diode 654 or another suitable device may be connected between the first switch 648 and the second node 652 to allow current flow from the bus voltage node 620 to the second node 652 and prevent current flow from the second node 652 back to the bus voltage node 620.

The communication components receive power via the second node 652. Closing the first switch 648 provides the bus voltage to the communication components. The processor module 624 may determine whether (or not) the battery 456 is connected to the battery terminals 460, for example, based on a battery status 688 generated by the monitoring module 684. The monitoring module 684 may sense whether a thermistor of the battery 456 is present and generate the battery status 688 based on whether the thermistor is present. For example, when the thermistor is not sensed, the monitoring module 684 may generate the battery status 688 to indicate that the battery 456 is not present, and vice versa. Other ways of determining whether the battery 457 is present, such as based on a voltage at a third node 656, may be less reliable or unreliable due to the presence of multiple current leakage paths.

A second diode 660 or another suitable device may be connected between the second node 652 and a fourth node 664 to which the battery 456 is (or would be) connected to allow current flow from the fourth node 664 to the second node 652 and prevent current flow from the second node 652 back to the fourth node 664. The first diode 654 and the second diode 660 allow current to be supplied to the second node 652 from either the battery 456 or the bus voltage node

620. A third diode 668 or another suitable device may be connected between the fourth node 664 and the third node 656 to allow current flow from the fourth node 664 to the third node 656 and prevent current flow from the third node 656 to the fourth node 664.

A second switch 672 is connected between the bus voltage node 620 and the third node 656. For example only, the second switch 672 may include a FET or another suitable type of switching device. A fourth diode 676 or another suitable device may be connected between the second switch 672 and the third node 656 to allow current flow from the bus voltage node 620 (when the second switch 672 is closed) to the third node 656 and prevent current flow from the bus voltage node 620 to the third node 656. The third diode 668 and the fourth diode 676 may act as a logic OR function and allow either the battery 456 or the bus voltage node 620 to supply the voltage at the third node 656.

The processor module 624 may open the second switch 672 when the battery 456 is not connected to the battery terminals 460. The processor module 624 may open the second switch 672, for example, to disable a battery charger module 680 and to prevent excessive current draw from the bus voltage node 620. Opening the second switch 672 may prevent voltage and current from appearing at the battery terminals 460 which could be accessible by a user. When the battery 456 is connected to the battery terminals 460, the processor module 624 may close the second switch 672 and open the first switch 648. In this manner, the communication components and other components of the diabetes management device 104 receive power via the fourth node 664 when the battery 456 is connected to the battery terminals 460, and the current draw from the bus voltage 620 is decreased.

The battery charger module 680 receives power from the bus voltage node 620 when the second switch 672 is closed. The battery charger module 680 selectively charges the battery 456 when the second switch 672 is closed. More specifically, the battery charger module 680 controls current flow to the battery 456.

The monitoring module 684 monitors one or more parameters. For example, the monitoring module 684 may monitor current flow to and/or from the battery 456, a voltage of the battery 456, a voltage at the fourth node 664, one or more temperatures of the battery 456, and/or other suitable parameters. The monitoring module 684 determines a state of charge (SOC) of the battery 456 based on one or more of the monitored parameters.

The battery charger module 680 controls current flow to the battery 456 based on a target current 692. Additionally or alternatively, the battery charger module 680 may control current flow to the battery 456 based on the SOC of the battery 456 and/or other input from the monitoring module 684. For example, the monitoring module 684 may selectively command the battery charger module 680 to not charge the battery 456 based on a temperature of the battery 456, and/or other suitable parameters.

A charge setting module 696 generates the target current 692. The charge setting module 696 may set the target current 692 based on signals from the multiplexer module 608 and/or the processor module 624. For example, the multiplexer module 608 may determine a predetermined value for the target current 692, and the processor module 624 may determine a present amount of power being consumed for operation of the diabetes management device 104. The charge setting module 696 may decrease the target current 692 from the predetermined value based on the present amount of power being consumed for operation of the diabetes management device 104. The processor module 624 and the battery charger module 680 may determine the predetermined value for the target current 692, for example, as a function of temperature of the battery 456, voltage of the battery 456, the SOC of the battery 456, and/or one or more other suitable parameters.

As stated above, the processor module 624 receives power via the bus voltage node 620 and/or the third node 656, and the communication components receive power via the second node 652 and/or the fourth node 664. In this manner, the processor module 624 is operational and the communication components can be operated, even at times when the battery 456 is not connected to the battery terminals 460.

The processor module 624 may control operation of the communication module 644 via a first driver 698. The processor module 624 may control operation of the backlight 636 via a second driver 700. The processor module 624 may control operation of the LED 444 via a third driver 704. The processor module 624 may control operation of the vibrator device 640 via a fourth driver 708. The processor module 624 may control operation of the display 408 via a fifth driver 712. The processor module 624 may control operation of the speaker 448 via a sixth driver 716.

A measurement engine 720 may receive power via the third node 656. Thus, the measurement engine 720 may only be operable when the battery 456 is connected to the battery terminals 460. The measurement engine 720 may also receive power via the bus voltage node 620 when the second switch 672 is closed by the processor module 624.

The processor module 624 may control operation of the measurement engine 720 via a seventh driver 724. The measurement engine 720 may determine a bG level of a blood sample when a bG test strip, such as the bG test strip 416, is inserted into the bG test strip port 420. The monitoring module 684 may also receive power via the third node 656, and the processor module 624 may control operation of the monitoring module 684 via an eighth driver 728.

Figure 7A:
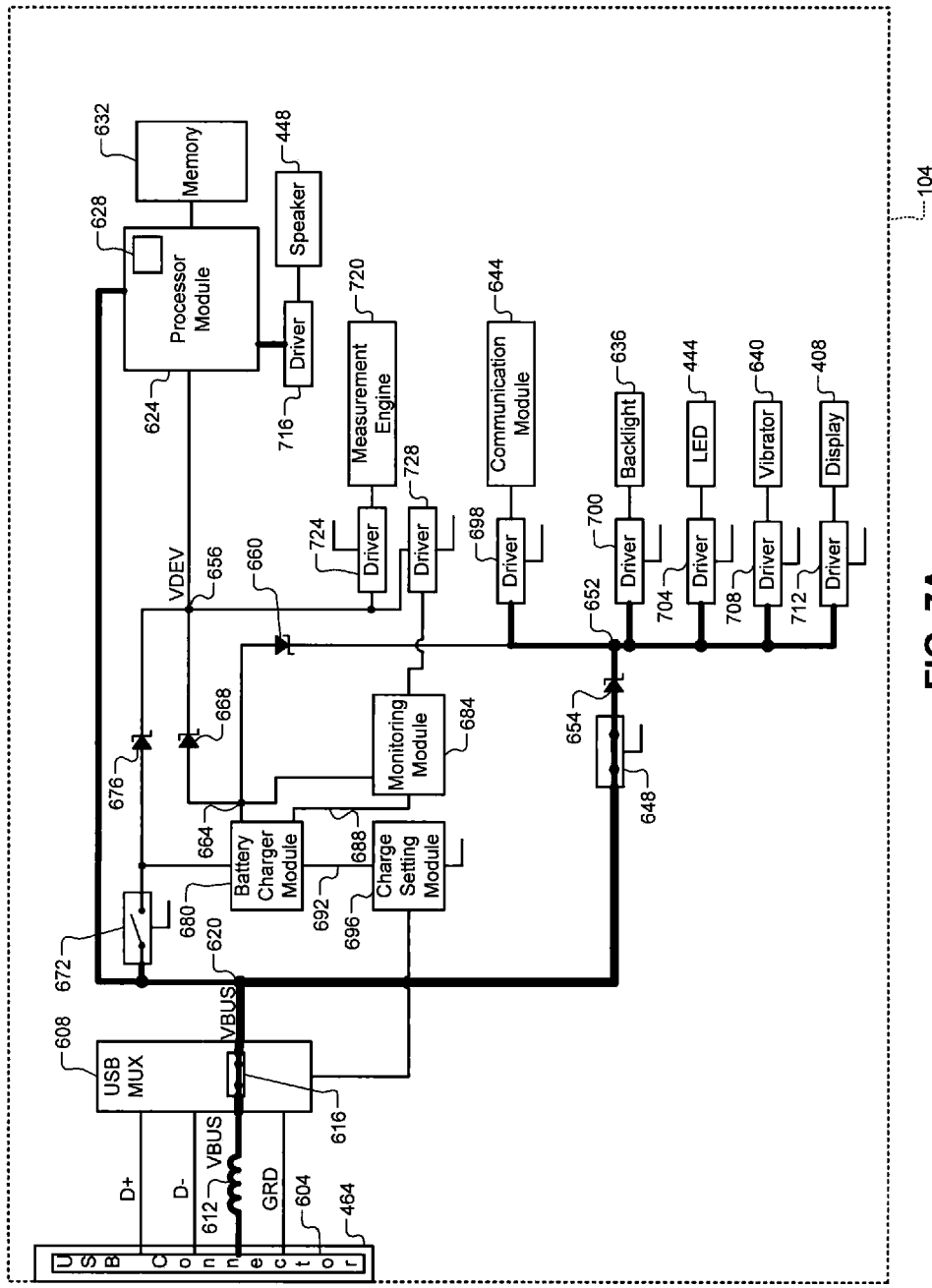
FIGS. 7A and 7B are illustrations of the functional block diagram of FIG. 6 with current paths through the example handheld diabetes management device.

FIG. 7A is a functional block diagram of the portion of the example implementation of the diabetes management device 104. The bold lines in FIG. 7A illustrate an example current path when the battery 456 is not connected to the battery terminals 460. The battery 456 is not shown in the example of FIG. 7A to emphasize this. The bold lines in FIG. 7B illustrate an example current path when the battery 456 is connected to the battery terminals 460.

Figure 7B:
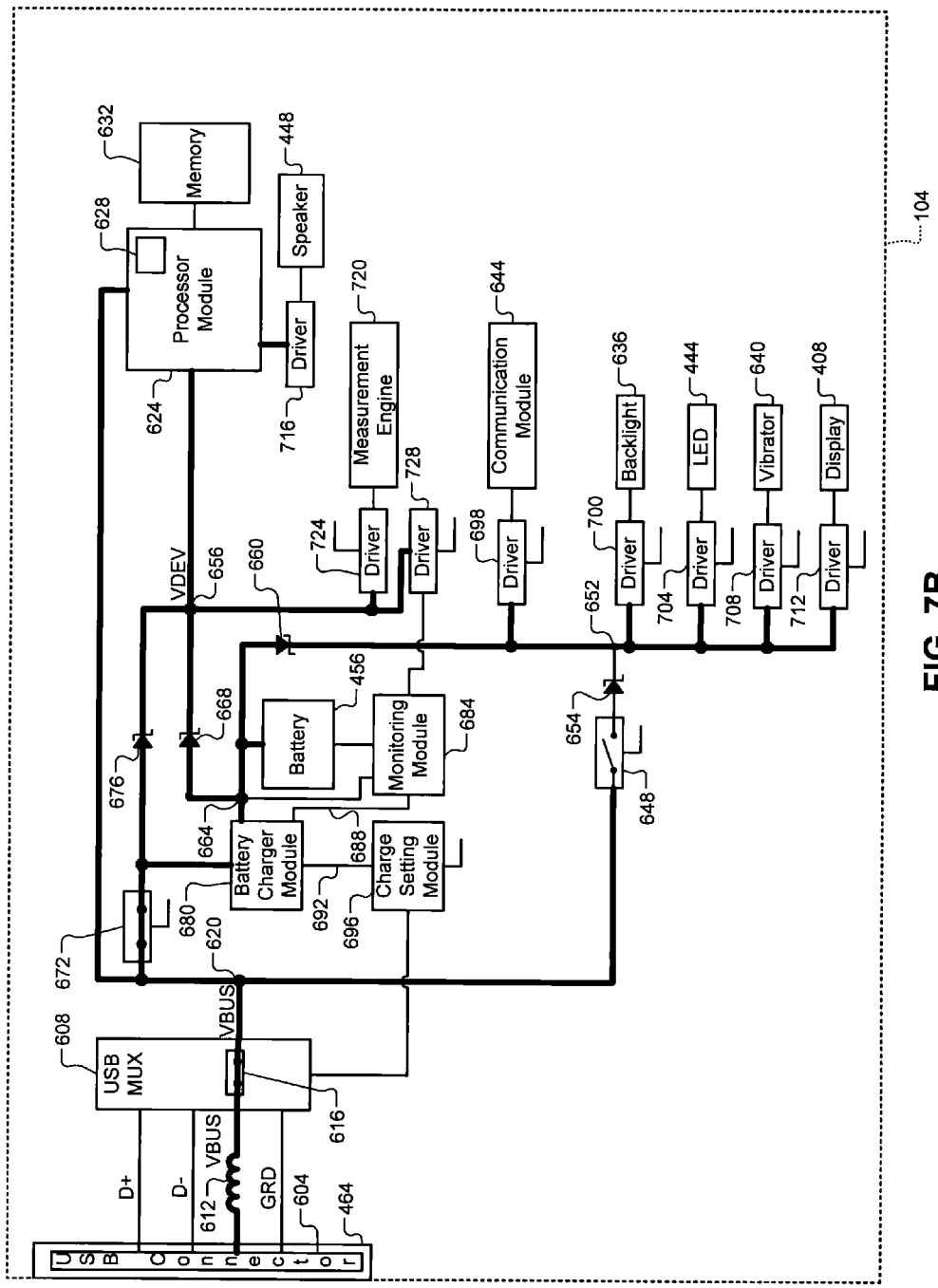

As illustrated by FIGS. 7A and 7B, the communication devices may be operated at times when the battery 456 is not connected to the battery terminals 460 and at times when the battery 456 is connected to the battery terminals 460. This may enable a user to perform various functions of the diabetes management device 104 even at times when the battery 456 is not connected to the battery terminals 460. For example, the user may review previously recorded diabetes management data (e.g., bG measurements, activity, insulin administration, food intake, etc.), communicate diabetes management data to another device (e.g., a personal computer), and perform other functions of the diabetes management device 104.

The measurement engine 720 and the monitoring module 684, however, may only be operated at times when the battery 456 is connected to the battery terminals 460 or when the processor module 624 closes the second switch 672 to power the measurement engine 720 and the monitoring module 684 at times when a special cable is connected to the USB port 464. Operation of the measurement engine 720 may be limited to times when the battery 456 is connected to the battery terminals 460, for example, to ensure that bG measurements are as accurate as possible. bG measurements taken while the battery 456 is not connected to the battery terminals 460 and power is received via the port 464 may be relatively less accurate. Operation of the monitoring module 684 may be limited to times when the battery 456 is connected to the battery terminals 460, for example, to limit unnecessary power consumption when the battery 456 is not present.

In a feature, a handheld diabetes management device that is at least partially functional while a battery of the handheld diabetes management device is disconnected from the handheld diabetes management device and power is supplied to the handheld diabetes management device via a universal serial bus (USB) connection is described. The handheld diabetes management device includes: a processor module including memory having instructions for executing functions of the handheld diabetes management device and a processor that selectively executes the instructions; and battery terminals that electrically connect the processor module with a re-chargeable battery when the re-chargeable battery is inserted within a battery compartment of the handheld diabetes management device. The handheld diabetes management device further includes: a receptacle that is configured in accordance with a universal serial bus (USB) standard and that receives a plug that is configured in accordance with the USB standard; at least one component for communicating information from the handheld diabetes management device to one of a user and another device; and a multiplexer module that receives power via the receptacle when the plug is connected with the receptacle and that selectively outputs power to a bus voltage node based on the power received via the receptacle. The processor module is directly connected to the bus voltage node and receives power from the bus voltage node when the re-chargeable battery is not connected to the battery terminals. The at least one component receives power via the bus voltage node when the re-chargeable battery is not connected to the battery terminals. The processor module controls application of power to the at least one component and operation of the at least one component when the re-chargeable battery is not connected to the battery terminals.

In further features, the multiplexer module includes a switching device that is connected between the receptacle and the bus voltage node. The switching device is open circuited when the power output to the bus voltage node is greater than a predetermined value.

In still further features, the handheld diabetes management device further includes a switching device that is connected between the bus voltage node and a second voltage node. The at least one component receives power from the second voltage node.

In other features, the processor module closes the switching device in response to a determination that the re-chargeable battery is not connected to the battery terminals.

In still other features, the handheld diabetes management device further includes a diode that is connected between the switching device and the second voltage node, that allows current flow from the switching device to the second voltage node, and that blocks current flow from the second voltage node to the switching device.

In further features, the handheld diabetes management device further includes a second switching device that is connected between the bus voltage node and a third voltage node. One of the battery terminals is connected to the third voltage node, and the processor module is also directly connected to the third voltage node.

In still further features, the handheld diabetes management device further includes: a blood glucose (bG) test strip port; and a bG measurement engine that is connected to the third voltage node and that measures a bG level of a bG test strip when the bG test strip is inserted into the bG test strip port.

The at least one component includes a communication module that communicates data from the handheld diabetes management to another device.

In other features, the re-chargeable battery is connected to the battery terminals, and the processor module selectively opens and closes the switching device and the second switching device. When the re-chargeable battery is not connected to the battery terminals, the processor module selectively opens and closes the switching device and the second switching device.

In still other features, when the re-chargeable battery is connected to the battery terminals, the processor module opens the switching device and closes the second switching device. When the re-chargeable battery is not connected to the battery terminals, the processor module closes the switching device and opens the second switching device.

In further features, the handheld diabetes management device further includes a battery charger module that receives power output from the second switching device and that, based on power consumption of the at least one component, controls current flow to the re-chargeable battery for re-charging the re-chargeable battery.

In still further features, the handheld diabetes management device further includes: a first current path from the re-chargeable battery to the processor module; and a second current path from the receptacle to the processor module via the multiplexer module and the bus voltage node. When the re-chargeable battery is not connected to the battery terminals, the processor module receives power via the second current path.

In other features, the handheld diabetes management device further includes: a first current path from the battery to the at least one component; and a second current path from the bus voltage node to the at least one component.

In still other features, in response to a determination that the re-chargeable battery is connected to the battery terminals, the processor module enables current flow through the first current path and disables current flow through the second current path; and in response to a determination that the re-chargeable battery is not connected to the battery terminals, the processor module disables current flow through the first current path and enables current flow through the second current path.

In further features, in response to a determination that the re-chargeable battery is not connected to the battery terminals, the processor module disables current flow through the first current path and enables current flow through the second current path.

In still further features, the at least one component includes a touchscreen display, a backlight of the touchscreen display, a visual indicator, and a vibrator device.

In another feature, a handheld diabetes management device that is at least partially functional while a battery of the handheld diabetes management device is disconnected from the handheld diabetes management device and power is supplied to the handheld diabetes management device via a universal serial bus (USB) connection is described. The handheld diabetes management device includes: a processor module including memory having instructions for executing functions of the handheld diabetes management device and a processor that selectively executes the instructions; battery terminals that electrically connect the processor module with a re-chargeable battery when the re-chargeable battery is inserted within a battery compartment of the handheld diabetes management device; and a receptacle that is configured in accordance with a universal serial bus (USB) standard and that receives a plug that is configured in accordance with the USB standard. The handheld diabetes management device further includes: at least one component for communicating information from the handheld diabetes management device to one of a user and another device; a multiplexer module that receives power via the receptacle when the plug is connected with the receptacle and that relays power from the receptacle to a bus voltage node, wherein the processor module is directly connected to the bus voltage node; a first current path from the battery to the at least one component; and a second current path from the bus voltage node to the at least one component. In response to a determination that the re-chargeable battery is connected to the battery terminals, the processor module enables current flow through the first current path and disables current flow through the second current path. In response to a determination that the re-chargeable battery is not connected to the battery terminals, the processor module disables current flow through the first current path and enables current flow through the second current path.

In further features, the handheld diabetes management device further includes a battery charger module that receives power from the bus voltage node and that, based on power consumption of the at least one component, controls current flow to the re-chargeable battery for re-charging the re-chargeable battery.

In still further features, the handheld diabetes management device further includes: a blood glucose (bG) test strip port; and a bG measurement engine that measures a bG level of a bG test strip when the bG test strip is inserted into the bG test strip port.

In another feature, a handheld diabetes management device that is at least partially functional while a battery of the handheld diabetes management device is disconnected from the handheld diabetes management device and power is supplied to the handheld diabetes management device via a universal serial bus (USB) connection is described. The handheld diabetes management device includes: a processor module including memory having instructions for executing functions of the handheld diabetes management device and a processor that selectively executes the instructions; battery terminals that electrically connect the processor module with a re-chargeable battery when the re-chargeable battery is inserted within a battery compartment of the handheld diabetes management device; and a receptacle that is configured in accordance with a universal serial bus (USB) standard and that receives a plug that is configured in accordance with the USB standard. The handheld diabetes management device further includes: at least one component for communicating information from the handheld diabetes management device to one of a user and another device; a multiplexer module that receives power via the receptacle when the plug is connected with the receptacle and that relays power from the receptacle to a bus voltage node, wherein the processor module is directly connected to the bus voltage node; a first switching device that is connected between the bus voltage node and a second voltage node, wherein the at least one component receives power from the second voltage node; and a second switching device that is connected between the bus voltage node and a third voltage node. One of the battery terminals is connected to the third voltage node, and the processor module is also directly connected to the third voltage node.

In further features, the handheld diabetes management device further includes: a blood glucose (bG) test strip port; and a bG measurement engine that is connected to the third voltage node and that measures a bG level of a bG test strip when the bG test strip is inserted into the bG test strip port. The at least one component includes a communication module that communicates data from the handheld diabetes management to another device. In response to a determination that the re-chargeable battery is connected to the battery terminals, the processor module closes the second switching device and opens the first switching device. In response to a determination that the re-chargeable battery is not connected to the battery terminals, the processor module opens the second switching device and closes the first switching device.

As used herein, the term "module" can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term "module" can include memory (shared, dedicated, or group) that stores code executed by the processor.

The term "code," as used above, can include software, firmware, and/or microcode, and can refer to programs, routines, functions, classes, and/or objects. The term "shared," as used above, means that some or all code from multiple modules can be executed using a single (shared) processor. In addition, some or all code from multiple modules can be stored by a single (shared) memory. The term "group," as used above, means that some or all code from a single module can be executed using a group of processors. In addition, some or all code from a single module can be stored using a group of memories.

The apparatuses and methods described herein can be implemented by one or more computer programs executed by one or more processors. The computer programs include processor-executable instructions that are stored on a non-transitory, tangible, computer readable medium. The computer programs can also include stored data. Examples of the non-transitory, tangible, computer readable medium include, but are not limited to, nonvolatile memory, magnetic storage, and optical storage.

The description is merely illustrative in nature and is in no way intended to limit the disclosure, its application, or uses. For purposes of clarity, the same reference numbers may be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A handheld diabetes management device that is at least partially functional while a battery of the handheld diabetes management device is discharged and power is supplied to the handheld diabetes management device via a universal serial bus (USB) connection, the handheld diabetes management device comprising:
   a housing having a blood glucose (bG) test strip port;
   a processor module carried in the housing, the processor module including memory having instructions for executing functions of the handheld diabetes management device and a processor configured for executing the instructions;
   battery terminals that electrically connected the processor module:

a re-chargeable battery electrically connected to the battery terminals;
a bG measurement engine coupled to the processor and the re-chargeable battery, the bG measurement engine configured to measure a bG level;
a receptacle that is configured in accordance with a universal serial bus (USB) standard;
a plug that is configured in accordance with the USB standard;
at least one component for communicating information from the handheld diabetes management device to one of a user and another device; and
a multiplexer module that receives power via the receptacle from the plug and prevents the measurement of the bG level,
a bus voltage node that selectively received power from the multiplexer module,
wherein the processor module is configured to directly connect to the bus voltage node and the processor module receives power from the bus voltage node based upon the re-chargeable battery being discharged,
wherein the at least one component receives power via the bus voltage node based upon the re-chargeable battery being discharged, and
wherein the processor module is configured to control application of power to the at least one component and operation of the at least one component based upon the re-chargeable battery is discharged.

2. The diabetes management device of claim 1 wherein the multiplexer module includes a switching device that is connected between the receptacle and the bus voltage node, and
wherein the switching device is open circuited when the power output to the bus voltage node is greater than a predetermined value.

3. The handheld diabetes management device of claim 1 further comprising,
a switching device; and
a second voltage node that is connected between the switching device and the bus voltage node, with the at least one component receiving power from the second voltage node.

4. The handheld diabetes management device of claim 3 wherein the processor module closes the switching device based upon determination that the re-chargeable battery is not connected to the battery terminals.

5. The handheld diabetes management device of claim 3 further comprising a diode that is connected between the switching device and the second voltage node, that allows current flow from the switching device to the second voltage node, and that blocks current flow from the second voltage node to the switching device.

6. The handheld diabetes management device of claim 3 further comprising,
a second switching device that is connected between the bus voltage node; and
a third voltage node connected to the second switching device, the bus voltage node, one of the battery terminals, and the processor module.

7. The handheld diabetes management device of claim 6 further comprising:
a blood glucose (bG) test strip port; and
a bG measurement engine that is connected to the third voltage node and that measures a bG level;
a bG test strip,
wherein the at least one component includes a communication module that communicates data from the handheld diabetes management to another device.

8. The handheld diabetes management device of claim 7 wherein:
the re-chargeable battery is connected to the battery terminals and the processor module is configured to open and close the switching device and the second switching device; and
the re-chargeable battery is not connected to the battery terminals and; the processor module is configured to open and close the switching device and the second switching device.

9. The handheld diabetes management device of claim 8 wherein:
the re-chargeable battery is connected to the battery terminals and; the processor module is configured to opens the switching device and closes the second switching device; and
the re-chargeable battery is not connected to the battery terminals and the processor module is configured to close the switching device and opens the second switching device.

10. The handheld diabetes management device of claim 1 further comprising:
a first current path from the re-chargeable battery to the processor module; and
a second current path from the receptacle to the processor module via the multiplexer module and the bus voltage node,
wherein, when the re-chargeable battery is not connected to the battery terminals, the processor module receives power via the second current path.

11. The handheld diabetes management device of claim 1 further comprising:
a first current path from the re-chargeable battery to the at least one component; and
a second current path from the bus voltage node to the at least one component.

12. The handheld diabetes management device of claim 11 wherein:
the processor module is configured to enable current flow through the first current path and disables current flow through the second current path based on a determination that the re-chargeable battery is connected to the battery terminals; and
the processor module is configured to disable current flow through the first current path and enables current flow through the second current path based on a determination that the re-chargeable battery is not connected to the battery terminals.

13. The handheld diabetes management device of claim 1 wherein the at least one component includes a touchscreen display, a backlight of the touchscreen display, a visual indicator, and a vibrator device.

* * * * *